United States Patent
Theodore et al.

(10) Patent No.: US 8,097,168 B2
(45) Date of Patent: *Jan. 17, 2012

(54) WASTEWATER PHOTO BIOMASS/ALGAE TREATMENT METHOD

(75) Inventors: Marcus G. Theodore, Salt Lake City, UT (US); Larry P. Wardle, Bountiful, UT (US)

(73) Assignee: Earth Renaissance Technologies, LLC, Salt Lake City, UT (US)

( * ) Notice: Subject to any disclaimer, the term of this patent is extended or adjusted under 35 U.S.C. 154(b) by 321 days.

This patent is subject to a terminal disclaimer.

(21) Appl. No.: 12/455,654

(22) Filed: Jun. 4, 2009

(65) Prior Publication Data

US 2009/0294354 A1    Dec. 3, 2009

Related U.S. Application Data

(63) Continuation of application No. 12/286,083, filed on Sep. 26, 2008, now Pat. No. 7,566,400, which is a continuation-in-part of application No. 11/893,557, filed on Aug. 14, 2007, now Pat. No. 7,455,773.

(51) Int. Cl.
*C02F 1/00* (2006.01)
(52) U.S. Cl. ............... 210/724; 210/747.1; 210/192; 210/743; 210/150; 210/151
(58) Field of Classification Search ............ 210/724, 210/747.1, 192, 743, 150–151
See application file for complete search history.

(56) References Cited

U.S. PATENT DOCUMENTS

| | | | |
|---|---|---|---|
| 4,304,673 A | 12/1981 | Reynolds et al. | |
| 4,340,489 A | 7/1982 | Adams et al. | |
| 4,764,353 A * | 8/1988 | Babjak et al. | 423/20 |
| 4,765,911 A | 8/1988 | Rasmussen | |
| 5,147,617 A * | 9/1992 | Touro et al. | 423/27 |
| 5,906,750 A | 5/1999 | Haase | |
| 2002/0153307 A1* | 10/2002 | Blais et al. | 210/631 |
| 2007/0048848 A1* | 3/2007 | Sears | 435/134 |

OTHER PUBLICATIONS

United Nations Environmental Programme Division of Technology, Industry, and Economics Newsletter and Technical Publications Management Series No. 1, "Bio-solids Management: An Environmentally Sound Approach for Managing Sewage Treatment Plant Sludge," 3p.

* cited by examiner

*Primary Examiner* — Chester Barry
(74) *Attorney, Agent, or Firm* — Marcus G. Theodore (57) ABSTRACT

A treatment method for wastewater employing sulfur dioxide and lime chemical dewatering technology in conjunction with an environmental photo biomass/algae biological treatment system growing photo biomass/algae to reduce dissolved solids, heavy metals, and ammonia in the wastewater to produce recovered treated wastewater for vegetation consumption, biofuel feedstock, and biofuel and carbon credits.

19 Claims, 5 Drawing Sheets

FIG. 5

WASTEWATER PHOTO BIOMASS/ALGAE TREATMENT METHOD

RELATED APPLICATIONS

This application is a continuation-in-part of prior application Ser. No. 12/286,083 filed Sep. 26, 2008 entitled "Wastewater Chemical/Biological Treatment Recovery Method and Apparatus", now U.S. Pat. No. 7,566,400, which is a continuation-in-part of application Ser. No. 11/893,557, filed on Aug. 14, 2007, now U.S. Pat. No. 7,455,773.

BACKGROUND OF THE INVENTION

1. Field

This invention comprises a wastewater treatment method employing chemical/mechanical dewatering and biological treatment technology for first propagating and recovering of photo biomass/algae to reduce BOD's and heavy metals to produce recovered treated wastewater suitable for reuse.

2. State of the Art

Various types of wastewaters are known. As used herein, it is principally directed to wastewaters containing organic and macronutrients suitable for growth of plants, algae, and photo biomass, including runoff from farmlands, domestic sewage from dwellings, business buildings, institutions, containing ground water, surface water, and/or storm water, and can include wastewater, having already undergone primary and secondary treatment according to conventional wastewater treatment plant processes. Consequently wastewater as used herein also includes other agricultural and industrial wastewaters containing similar nutrients and requiring similar conditioning, disinfection, and deodorizing to provide feedstock for growing photo biomass/algae. One source of wastewater is that present in sewage treatment gathering systems, which are processed by various methods. Most large municipal systems employ a series of settling ponds sequentially concentrating the solids contained in wastewater either with or without polymers for separation from liquids via mechanical separation means, such as belt presses. To produce a clean effluent that can be safely discharged to watercourses, wastewater treatment operations use three or four distinct stages of treatment to remove harmful contaminants; according to the United Nations Environmental Programme Division of Technology, Industry, and Economics Newsletter and Technical Publications Freshwater Management Series No. 1, *"Biosolids Management: An Environmentally Sound Approach for Managing Sewage Treatment Plant Sludge"*.

Preliminary wastewater treatment usually involves gravity sedimentation of screened wastewater to remove settled solids. Half of the solids suspended in wastewater are removed through primary treatment. The residual material from this process is a concentrated suspension called primary sludge, subsequently undergoing additional treatment to become bio-solids.

Secondary wastewater treatment is accomplished through a biological process, removing biodegradable material. This treatment process uses microorganisms to consume dissolved and suspended organic matter, producing carbon dioxide and other by-products. The organic matter benefits by providing nutrients needed to sustain the communities of microorganisms. As microorganisms feed, their density increases and they settle to the bottom of processing tanks, separated from the clarified water as a concentrated suspension called secondary sludge, biological sludge, waste activated sludge, or trickling filter humus. By breaking down the sludge, the wastewater system loses energy and increases carbon dioxide emissions.

Tertiary or advanced treatment is used when extremely high-quality effluent is required, including direct discharge to a drinking water source. The solid residual collected through tertiary treatment consists mainly of chemicals added to clean the final effluent, which are reclaimed before discharge, and therefore not incorporated into bio-solids. Tertiary or advanced treatment does not reduce the treated wastewater brine content, requiring energy intensive Quaternary brine treatment removal using reverse osmosis and distillation, and other methods.

Combined primary and secondary solids comprise the majority of material used at municipal plants for bio-solids production. Careful management throughout the entire treatment process allows plant operators to control the solids content, nutrient value and other constituents of bio-solids.

The Municipal Sludge-to-Bio-solids Treatment Process

Three important factors must be addressed through further processing before this material can be utilized: (1) pathogen levels, (2) presence of potentially harmful industrial contaminants, and pharmaceuticals and personal care products, and (3) water content.

The principal process employed to convert municipal sludge into bio-solids is called stabilization. Stabilization accelerates the biodegradation of organic compounds, reduces the microbial population including pathogens, and renders the material microbiologically safe for some types of agricultural use. Biological stabilization uses aerobic or anaerobic treatment to reduce the organic content of solids through controlled biodegradation. Chemical stabilization does not reduce the quantity of biodegradable organic matter in solids, but creates process conditions inhibiting microorganisms, thereby slowing the degradation of organic materials and reducing odors. The most common chemical stabilization procedure is to elevate the pH level of the solids using lime or other alkaline materials. Thermal drying and composting can be used to stabilize bio-solids. Full pasteurization of bio-solids is not needed when the primary use is cropland application. Any potential risk to human health due to exposure to pathogens is eliminated through proper controlled application procedures and in-situ microbial decomposition.

The presence of contaminants in the sludge or bio-solids arising from industrial discharges is a more challenging problem and may be the deciding factor in determining the choice of a utilization disposal option. Put simply, many industries have habitually used the sewer system as a convenient and low-cost way to discharge hazardous wastes. The contaminants accumulate in the biomass and sludge, and can render the material unfit for any beneficial use. The most common options used for disposal of this contaminated material are landfill or incineration, particularly where heavy metals or pathogens are still present in the sludge. The cost is usually borne by the municipality rather than the hazardous waste generator. Bio-solids utilization is a good, environmentally sustainable option when the wastewater is from municipal sources only, or when a fully enforced industrial pre-treatment and discharge control system is in place. The decision to select an environmentally sustainable approach to bio-solids management can be used very effectively to review and correct polluting practices up-stream that should not be taking place.

The final concern is the water content of the bio-solids product. Primary and secondary sludge generally contain no more than four percent solids, and the storage and transportation costs of this semi-liquid material limit the application to nearby farmland. Processes to remove water from solids, therefore, are common in bio-solids production. The simplest method for removing water is gravity thickening, involving concentration by simple sedimentation. Allowing sufficient time for solids to settle in tanks can increase suspended solids concentration to five or six percent. Thickening can include flotation processes, gravity drainage belts, perforated rotating drums, and centrifuges. Nothing is added to bio-solids during the gravity thickening processes.

Dewatering is another standard method of water removal in bio-solids production. Simple dewatering involves containment of wastewater solids in drying beds or lagoons, where gravity, drainage, and evaporation remove moisture. More often, dewatering involves mechanical equipment including filter presses, vacuum filters, and centrifuges. Mechanically dewatered solids typically contain between 20% and 45% solids. Finally, drying processes can be used to remove even larger volumes of water from bio-solids. Thermal drying with direct or indirect dryers followed by polarization can remove virtually all water and stabilize bio-solids to the point of full compliance with any regulatory requirement. This method is used where a viable commercial market exists for the pelletized product, and drying energy costs can be passed on.

Thus a particular wastewater treatment facility design is highly dependent upon the wastewater inflows and sludge composition and the discharge and treatment permitting restrictions and plant objectives. Oftentimes these plant designs employ thermophilic and other digestion processes to decompose the sludge as part of the separation process. For example, Haase, U.S. Pat. No. 5,906,750 issued May 25, 1999 discloses a method for dewatering of sludge previously digested by a thermophilic digestion process employing polymers. The polymers are extremely hydrophilic as they agglomerate fine particles for separation from the wastewater in the belt presses. This gelatinous mechanically separated mass is then usually land filled or admixed with other fuels for burning, and may contain significant pathogens and heavy metals. Once deposited and covered, these landfills do not breakdown rapidly. They comprise large deposits of unstable gelatinous soil, which acts as a breeding ground for pathogens. If these separated solids are treated with chlorine for pathogen kill, chlorinated carcinogens often result, creating a different environmental hazard.

The mechanically separated gray water by-product is usually not treated and is then used for agricultural application, or dumped into a body of water for dilution. If treated with chlorine to kill pathogens before land application or dumping, its usage for agricultural purposes is less than ideal as any residual chlorine acts as an herbicide.

In addition, mechanical sludge separation typically requires a large series of settling ponds with wastewater residence times therein typically from 24 to 48 hours, depending upon the weather and nature of the sludge processed. Typically, landfill and polymer costs represent approximately 30 percent of wastewater treatment costs. This long dwell time results in further concentrations of the brines.

Other mechanical filtration methods provide sludge separation, but require continual unplugging of the filters; generating significant ongoing costs of filter replacement and declining effectiveness as the filter becomes plugged with the separated solids.

Conventional mechanical sewage separation plants are thus designed to breakdown and separate the wastewater components, and vent CO2 into the air. They also use competing bacterial, which may interfere with the propagation of photo biomass/algae, and are capital and energy intensive and have to be operated within environmental discharge and landfill permit constraints. Consequently, they are not routinely used as a nutrient source to propagate algae and photo biomass. They require significant upfront capital investment and may result in long term environmental clean-up and remediation costs. As urban populations being served grow and landfill costs increase, these plants seldom meet permitting constraints without significant upgrades in design, particularly with respect to pathogen gray water discharge and the negative impacts caused by mountains of gelatinous solids.

Other chemical wastewater treatment methods employ chemical agglomeration and disposal methods, such as Adams et al., U.S. Pat. No. 4,340,489 issued Jul. 20, 1982 wherein wastewater is treated with sufficient sulfurous acid to effectuate disinfection. Polymers and other separation methods are then employed to remove the solids. Reynolds et. al., U.S. Pat. No. 4,304,673 issued Dec. 8, 1981 is another wastewater treatment process employing chemicals to disinfect sewage sludge continuously in a similar manner as Adams et al. Rasmussen, U.S. Pat. No. 4,765,911, issued Aug. 23, 1988 is another two-stage chemical treatment process for treating aerobic or anaerobic sewage sludge. These chemical wastewater treatment methods are not package systems, use chemicals at concentrations, which retard photo biomass/algae production, rely heavily on the use of polymers, and do not address the issues of BOD's and ammonia in treated wastewater or brine disposal methods.

Thus, there remains a need for a method and apparatus, able to be rapidly installed either as a standalone or retrofit package wastewater treatment system to chemically treat and recover wastewater solids and liquids for subsequent environmental biological usage and polishing. The treatment method described below provides such an invention suitable for first raising algae and photo biomass from wastewater to produce recovered treated wastewater with reduced BOD's and heavy metals suitable for reuse.

SUMMARY OF THE INVENTION

The present invention comprises a wastewater treatment method employing chemical dewatering and biological treatment technology for first propagating and recovering of photo biomass/algae to reduce BOD's and heavy metals to produce recovered wastewater suitable for reuse. It is modular and can be rapidly installed at an existing wastewater treatment plant for chemical dewatering and disinfection to condition wastewater first to raise photo biomass/algae for reuse and to further clean the wastewater for reuse.

Method

The method comprises chemically treating the wastewater containing solids, photo biomass/algae nutrients, and heavy metals with sulfur dioxide to condition the wastewater and separate the solids. The sulfurous acid, ($H_2SO_3$), dissociates to produce $H^+$, bi-sulfite ($HSO_3^-$), sulfite ($SO_3^=$), and free $SO_2$ species in solution, all hereinafter referred to as sulfurous acid. Conditioning the liquid fraction to kill competing bacteria and pathogens prevents loss of the nutrients and energy needed for growth of photo biomass/algae in a bioreactor. This also reduces the production of $CO_2$ by the competing bacteria and pathogens breaking down the nutrients.

Conditioning of the solids is defined as treating the filtered solids with sufficient $SO_2$ ensuring they will chemically dewater when allowed to drain, forming a fairly dry solid with a BTU content approximating wood chips or shavings. Conditioning of the solids generally results in a color change of the solids from a dark brown to a lighter gray brown color.

Before sulfurous acid treatment, the wastewater containing nutrients and solids may be aerated to kill viruses and oxidize unwanted chemicals. The subsequent sulfur dioxide treatment acts as a scavenger molecule to remove excess oxygen and act as a reducing agent to inactivate many unwanted pharmaceuticals and chemicals, which may affect subsequent algae growth. This oxidation/reduction cycle is particularly employed where pharmaceuticals and other drugs are present in the wastewater, which may affect algae and aquatic plant production.

The $SO_2$ treated liquid wastewater fraction generally changes from a greenish color to a lighter gray brown colloidal suspension color. The malodorous smell of the raw wastewater is concomitantly replaced by a slight acidic smell. Consequently, the conditioning point can easily be determined by injecting more and more $SO_2$ into the wastewater until the color and odor changes occur—usually observed at a pH of approximately between 1.5 and 3.5, depending upon dwell time. If the color changes are too faint, the pH can be measured instead. Sulfur dioxide has lone electron pairs, allowing it to act as a Lewis base. Additionally it can act as a Lewis acid. The dissolved $SO_2$ gaseous content varies with temperature. For example, the grams/liter of dissolved sulfur dioxide in water at 20 degrees C. is 106.4 gm/L. It is 55.4 gm/L at 40 degrees. It is 32.5 gm/L at 60 degrees, and 21.3 gm/L at 80 degrees. Consequently, this sulfurous acid treated wastewater system with free $SO_2$/sulfurous acid/bi-sulfite/sulfite present in solution at a low pH forms a complex liquid/gas/solid phase chemistry system where reactions are difficult to describe and quantify exactly, but the above sulfurous acid wastewater conditioning endpoints are distinct. The conditioning of the wastewater and solids via oxidation/reduction reactions thus form self adhering solids, shedding water upon drying, and disinfected wastewater with high plant and algae nutrients at the point where the odor reduction and color changes of the conditioned solids and liquids occur. Heavy metals, in particular, are acid leached from the solids into the aqueous fraction, as nutrients to promote algae bloom or eutrophication for heavy metals removal from the recovered liquid fraction. This leaves a heavy metals free separated solid suitable for land application.

After sulfur dioxide-treatment, the chemically dewatered solids are separated and then disposed of consistent with applicable discharge permits. The resultant chemically treated wastewater liquid fraction is then neutralized with lime or calcium carbonate to inactivate the biocidal properties of the sulfurous acid at a pH suitable for raising aqueous plants, algae, and photo biomass, hereinafter all referred to as photo biomass/algae. If heavy metals are present in amounts detrimental to the algae in the filtered $SO_2$ treated liquid fraction, the treated wastewater pH can first be raised to precipitate and separate out the heavy metals contained in the wastewater resulting in metal free filtrate. Ideally, this process is conducted prior to subsequent biosolids consolidation. A pH of up to 11 will precipitate all of the heavy metals as metal hydroxides. If there are heavy metal hydroxides, which become more soluble at higher pH levels, they are sequentially removed with filtration. For example, at higher pH levels, chromium and possibly iron and aluminum become more soluble as $Fe(OH)_4^-$ or $Al(OH)_4^-$ or $Cr(OH)_4^-$ ions. They therefore are removed at the pH at which they precipitate before the pH is then raised higher to remove other heavy metal hydroxides.

The final high pH is then acid reduced for environmental biological algae treatment—usually to a pH range of approximately 6 to approximately 8. Other factors in the selection of this pH are the soil alkalinity in a region, and whether the treated wastewater will be land applied or discharged to an aqueous environment.

The high pH around 11 causes ammonia to separate into a gas for possible removal through scrubbing where the ammonia level in the acid treated wastewater is too high for secondary recovery water re-usage. However, for most $SO_2$ treated wastewaters, the biological removal of ammonia via plant and algae consumption is sufficient.

The photo biomass/algae are contained in an environmental photo biomass/algae biological system, such as a bioreactor or open impoundment. These photo biomass/algae organisms remove BOD's and heavy metals, as they grow to a mass suitable for separation and reuse.

When treating the incoming raw wastewater entering a sewage treatment plant, the resulting sulfur dioxide-treated, pH adjusted nutrients in wastewater are continuously generated, of a consistent composition, and provide a good source for photo biomass/algae cultivation, which consumes and removes not only the nutrients from the wastewater, but absorbs CO2 as they form sugars and lipids. The treatment process thus generates carbon credits, a biofuel feedstock and a recoverable wastewater for reuse.

According to Wikepaedia, Algae Fuels, http://en.wikipedia.org/wiki/Algae_fuel, algae grow rapidly and can have a high percentage of lipids, or oils. They can double their mass several times a day and produce at least 15 times more oil per acre than alternatives such as rapeseed, palms, soybeans, or jatropha. They can grow 20 to 30 times faster than food crops. Thus, when used to grow biofuel feedstock, farm acreage is freed up for raising food crops. However, the hard part about photo biomass/algae production is growing the algae in a controlled way and harvesting it efficiently. Live bacteria and viruses must also be killed to prevent their competing with the algae for the nutrients, in the manner discussed above.

Algae are a large and diverse group of simple, typically autotrophic organisms, ranging from unicellular to multicellular forms. The largest and most complex marine forms are called seaweeds. They are photosynthetic, like plants, and "simple" because they lack the many distinct organs found in land plants. For that reason they are currently technically excluded from being considered plants. However, past usage of the term "aquatic vegetation" or "aquatic plants" often includes algae, depending on the context.

Though the prokaryotic Cyanobacteria (commonly referred to as Blue-green Algae) were traditionally included as "Algae" in older textbooks, many modern sources regard this as outdated and restrict the term Algae to eukaryotic organisms. All true algae therefore have a nucleus enclosed within a membrane and chloroplasts bound in one or more membranes. Algae constitute a paraphyletic and polyphyletic group, as they do not include all the descendants of the last universal ancestor nor do they all descend from a common algal ancestor, although their chloroplasts seem to have a single origin.

Algae lack the various structures that characterize land plants, such as phyllids and rhizoids in nonvascular plants, or leaves, roots, and other organs that are found in tracheophytes. Many are photoautotrophic, although some groups contain members that are mixotrophic, deriving energy both from photosynthesis and uptake of organic carbon either by osmotrophy, myzotrophy, or phagotrophy. Some unicellular species rely entirely on external energy sources and have limited or no photosynthetic apparatus. For purposes of this patent application, the term "photo biomass/algae" will refer to all unicellular and multicellular photoautotrophic, mixotrophic and paraphyletic and polyphyletic forms, and photo biomass including seaweeds, and cyanobacteria and photosynthetic bacteria as well as aqueous photosynthetic plants suitable for consuming nutrients from wastewater and use as biofuel feedstock.

Nearly all algae have photosynthetic machinery ultimately derived from the Cyanobacteria, and so produce oxygen as a by-product of photosynthesis, unlike other photosynthetic bacteria such as purple and green sulfur bacteria.

The preferred algae for biofuel feedstock is one, which is high in lipids and algae oils, such as *botryococcus braunii, chlorella, dunaliella tertiolecta, graciaria, pleurochrysus carterae, sargassum*, and other micro algae—all of which will be referred to hereafter as "algae feedstock". Algae are made up of eukaryotic cells. These are cells with nuclei and organelles. All algae have plastids, the bodies with chlorophyll that carry out photosynthesis. But the various lines of algae have different combinations of chlorophyll molecules. Some have only Chlorophyll A, some A and B, while other lines, A and C.

According to the Oilgae newsletter website, http//www.oilgae.com/algae/comp/comp.html, all algae primary comprise of the following, in varying proportions: Water is the predominant component of algae. Next are Proteins, Carbohydrates, Fats and Nucleic Acids. While the percentages vary with the type of algae, there are algae types that are comprised up to 40% of their overall mass by fatty acids. It is this fatty acid (oil) that is extracted and converted into biodiesel using conventional methods, or directly along with the cellulose walls into a fuel additive using the method of the present invention. The table below identifies the chemical composition of various dried algae strains

TABLE 1

Chemical Composition of Algae Expressed on A Dry Matter Basis (%)

| Strain | Protein | Carbohydrates | Lipids | Nucleic acid |
|---|---|---|---|---|
| *Scenedesmus obliquus* | 50-56 | 10-17 | 12-14 | 3-6 |
| *Scenedesmus quadricauda* | 47 | — | 1.9 | — |
| *Scenedesmus dimorphus* | 8-18 | 21-52 | 16-40 | — |
| *Chlamydomonas rheinhardii* | 48 | 17 | 21 | — |
| *Chlorella vulgaris* | 51-58 | 12-17 | 14-22 | 4-5 |
| *Chlorella pyrenoidosa* | 57 | 26 | 2 | — |
| *Spirogyra* sp. | 6-20 | 33-64 | 11-21 | — |
| *Dunaliella bioculata* | 49 | 4 | 8 | — |
| *Dunaliella salina* | 57 | 32 | 6 | — |
| *Euglena gracilis* | 39-61 | 14-18 | 14-20 | — |
| *Prymnesium parvum* | 28-45 | 25-33 | 22-38 | 1-2 |
| *Tetraselmis maculata* | 52 | 15 | 3 | — |
| *Porphyridium cruentum* | 28-39 | 40-57 | 9-14 | — |
| *Spirulina platensis* | 46-63 | 8-14 | 4-9 | 2-5 |
| *Spirulina maxima* | 60-71 | 13-16 | 6-7 | 3-4.5 |
| *Synechoccus* sp. | 63 | 15 | 11 | 5 |
| *Anabaena cylindrica* | 43-56 | 25-30 | 4-7 | — |

Source: Becker, (1994)

Algal-oil is very high in unsaturated fatty acids. Some UFA's found in different algal-species include:
  Arachidonic acid(AA)
  Eicospentaenoic acid(EPA)
  Docasahexaenoic acid(DHA)
  Gamma-linolenic acid(GLA)
  Linoleic acid(LA)

The particular algae feedstock is therefore selected for its chemical composition, as well as abilities to rapidly grow at a particular location.

Three methods are generally employed to raise algae and photo biomass from the sulfur dioxide-treated wastewater:
  Photo Bioreactors Most companies pursuing algae as a source of biofuels are pumping nutrient-laden water through plastic tubes (called "bioreactors") that are exposed to sunlight (and so called photo bioreactors or PBR). Running a PBR is more difficult than an open pond, and more costly. Algae can also grow on marginal lands, such as in desert areas where the groundwater is saline, rather than utilize fresh water. The difficulties in efficient biodiesel production from algae lie in finding an algal strain with a high lipid content and fast growth rate that isn't too difficult to harvest, and a cost-effective cultivation system (i.e., type of photo bioreactor) that is best suited to that strain. There is also a need to provide concentrated $CO_2$ to turbo charge the production in a PBR.

Closed Loop System

Another obstacle preventing widespread mass production of algae for biofuel production has been the equipment and structures needed to begin growing algae in large quantities. Diversified Energy Corporation avoided this problem by taking a different approach, and growing the algae in thin walled polyethylene tubing called Algae Biotape (developed by XL Renewables, Inc), similar to conventional drip irrigation tubing, which can be incorporated into a normal agricultural environment. In a closed system (not exposed to open air) there is not the problem of contamination by other organisms blown in by the air. The problem for a closed system is finding a cheap source of sterile carbon dioxide ($CO_2$). Several experimenters have found the $CO_2$ from a smokestack works well for growing algae. To be economical, some experts think that algae farming for biofuels will have to be done next to power plants, where they can also help soak up the pollution.

Open Pond

Heretofore open-pond systems for the most part have been given up for the cultivation of algae with high-oil content. Open pond-systems are dependent upon the hardiness of the strain chosen. Using a local algae or photo biomass strain near the wastewater treatment plant ensures a strain able to withstand wide swings in temperature and pH, and competition from invasive algae and bacteria. Open systems using a monoculture are also vulnerable to viral infection, which is avoided by the oxygen/sulfur dioxide wastewater treatment oxidation/reduction cycle of the present invention. The energy that a high-oil strain invests into the production of oil is energy that is not invested into the production of proteins or carbohydrates, usually resulting in the species being less hardy, or having a slower growth rate. Algal species with lower oil content, not having to divert their energies away from growth, have an easier time in the harsher conditions of an open system. Thus, to raise algae in the digesters of a wastewater treatment plant for biofuel feedstock, it is preferred to utilize the hardiest local specie to optimize growth and production, and later supplement its oil content in the biofuel production process.

The advantage of the present method over other methods attempting to use conventional wastewater treatment for raising algae is that these other methods do not feed algae directly, but must first process the solids and wastewater by bacteria, through anaerobic digestion. If the treated waste water is not processed before it reaches the algae, it will contaminate the algae in the reactor, and at the very least, kill much of the desired algae strain. Conversely, the present method immediately disinfects the wastewater avoiding loss of energy in the nutrients and the need for anaerobic digestion, which often takes up to 21 days.

When operating at a wastewater treatment plant, the conventional wastewater treatment plant's existing aerobic and anaerobic digesters can be inactivated and converted into open environmental photo biomass/algae biological systems without incurring significant added capital costs, other than employing an independent biomass harvesting filtration system. These digesters normally grow bacteria to break down nitrates and agglomerate solids to drop to the bottom for subsequent separation and collection. Instead of bottom separation, the digesters are adapted to grow algae and photo biomass in their top two foot layer where they float and grow in sunlight. The photo biomass/algae blooms and is periodically collected by skimming or slurry pumping the top algae layer into a water separation filter system, such as woven bags or centrifuges to remove the photo biomass/algae and provide reduced BOD water for reuse as recovered wastewater. In another design variation, the entering wastewater is slowly added at the bottom of the converted digester forcing the top algae growth layer continually to overflow over the top of the digester into a collection basin for recovery. This continual removal of the top layers of the algae exposes underlying new growth to sunlight for continuous propagation of biomass.

Although these anaerobic and aerobic digesters usually are too deep for optimally growing algae of the upper two feet exposed to light in shallower ponds, the added depth has value in better absorbing $CO_2$ flu gas injected at the bottom to promote aquatic plant and algae growth. The heat from the flu gas is used to raise the temperature of the ponds, which promotes algae growth.

A preferred universal chemical/biological wastewater treatment method for wastewater streams with dissolved and un-dissolved solids able to be chemically dewatered by the injection of $SO_2$ to condition and deodorize both the liquids and solids for recovery comprises:

a. screening wastewater inflows through filtration means to separate and capture coarse solids to produce filtered liquids, b. injecting sulfur dioxide at a pH generating sufficient free $SO_2$, bi-sulfite, and sulfite into the filtered liquids to deodorize and condition the solids and liquids to form a sulfurous acid-treated wastewater stream with dissolved nutrients and metals, and conditioned solids, c. holding the sulfurous acid treated wastewater stream within the same vessel where the sulfur dioxide was injected, or a separate detention vessel, for a period of time until odors are suppressed, the suspended solids are conditioned to agglomerate and separate from the liquid fraction upon separation; and the dissolved solids, ammonia, and metals in the wastewater liquid fraction are disinfected, d. separating and disposing of the conditioned suspended solids from the wastewater liquid fraction, e. pH adjusting the wastewater liquid fraction by raising its pH to neutralize the biocidal properties of the free $SO_2$, sulfite, and bisulfite and provide a pH adjusted wastewater with the required pH for subsequent environmental algae/photo biomass biological treatment, and f. using the pH adjusted wastewater liquid fraction for raising algae, aquatic plants, and other photo biomass in open ponds, photo bioreactors, or closed loop systems to reduce BOD and heavy metal levels, g. harvesting the algae and photo biomass periodically for biofuel feedstock, and other uses producing a recovered treated wastewater, and h. reusing the recovered treated wastewater By utilizing sulfur dioxide and pH adjusted conditioned wastewater to propagate algae and other photo biomass, this method of treatment assimilates carbon dioxide from the air, and reduces the overall concentration and salt load currently being added by conventional wastewater treatment facilities into rivers and natural waterways. This recovered treated wastewater serves as a substitute alternative water supply reducing the need to take water from a river or deep well aquifers. By leaving more water in natural waterways, water quality is improved as salts remain more diluted downstream. If slightly acidified and land applied, any salts within the recovered treated wastewater are spread and leached deeper and more evenly over a wider area of land and/or watershed. This slows down and lessens the concentration of salts reentering a river system and can improve water quality during times of drought. Although heavy rain events may cause some of these land applied salts to be eventually washed back into the river, it occurs at a time when they are significantly diluted by rainwater or runoff. As a viable irrigation alternative to pumping water from deep wells, it can also help to prevent subsurface salts from being brought back to the surface where they can re-enter and co-mingle with the existing surface flow of a river.

In addition, many pharmaceuticals and drugs contained in the wastewater are deactivated so that they do not contaminate other water sources.

The disinfection chemicals used for chemical dewatering are anhydrous or hydrous sulfur dioxide, which provide rapid water/solids separation. To minimize operator exposure to sulfur dioxide, preferably a sulfurous acid generator is employed. Sulfur dioxide chemical dewatering generates self-agglomerating solids, which can be more readily separated from the liquid fraction via conventional screens or drying beds without the need for polymers. Sulfur dioxide dissolves readily in water requiring little mixing. Disinfected sulfur dioxide separation of wastewater and dewatering of the resultant solids typically takes 20 minutes to an hour compared to the 24 and 48 hours separation time with present mechanical concentrators. The actual dwell time required is dependent upon the alkalinity of the wastewater, and the porosity of the separation equipment screens sand filters or bags employed. Generally, it is easier to move the solids in a 1% to 3% slurry, so the $SO_2$ may be injected into the wastewater and held the minimal time for the solids to reach the particle size in a pipeline or dwell tank to effectuate an initial separation for subsequent collection in an equipment filter screen, sand filter, or drain bag. The solids then further agglomerate and dewater more completely within the equipment screens, filters or bags. For those exceptional sludges, which may require initial agglomeration assistance, acid resistant polymers, such as cationic copolymers of acrylamide with a cationic monomer, or cationically modified acrylamide or polyamine, may be employed may be added to the sulfurous acidified wastewater. Other polyquaternary amines, which are pH insensitive and function well over a broad pH, may also be employed.

Because of the fast reaction time, the size of the treatment vessels and drain bags is materially less so land usage is minimized. Chemically treated wastewater methods provide greater flexibility in equipment separation designs, which result in further cost savings. Nor is there usually any need for adding polymers first to agglomerate the solids as is the case with conventional belt presses and centrifugal or mechanical separators used in conventional mechanical sewage treatment plants, providing additional cost savings.

Material handling costs are also reduced. Sulfur dioxide batch treatment generates an initial separated solid having a water content of 30% to 40% in approximately 5 to 10 minutes, depending on composition. These solids, after separation, are then allowed to continue to chemically dewater until a solids composition having water content as low as approximately 4% is effectuated. If the chemical exposure is extended to approximately 20 minutes to insure disinfection, odor generation during the remainder of the treatment and disposal process is avoided. Sulfur dioxide also acid leaches the heavy metals into the liquid fraction for ease of removal via the subsequent addition of lime.

This rapid sulfur dioxide injection and separation generating self-agglomerating solids and heavy metals in the liquid fraction enables the use of much smaller gas injection and separation equipment than conventional mechanical dewatering systems. The sulfur dioxide dewatering equipment can be installed in modules, as needed. Thus, sulfur dioxide dewatering requires lower capital equipment cost investment, and has comparable or somewhat higher handling costs.

Apparatus

One embodiment of a wastewater treatment apparatus comprises a package hybrid chemical/mechanical/biological dewatering sewage treatment apparatus for wastewater inflow streams, which can be chemically dewatered by the injection of hydrous or anhydrous sulfur dioxide to rapidly agglomerate and separate solids from wastewater. Bottled $SO_2$ may be employed to provide the supply of hydrous sulfur dioxide, which is associated with a gas diffuser to gasify the wastewater.

A reaction vessel, such as a pipe or flow through vessel, is in communication with the wastewater inflow streams. A mixer is mounted within a reaction vessel and is associated with the supply of bottled sulfur dioxide for chemically injecting and admixing sufficient sulfur dioxide into the wastewater inflows until the solids agglomerate and separate from the liquid fraction of the wastewater. Alternatively, the wastewater inflows may be directed through a sulfur generator for admixing with the $SO_2$ into the wastewater. The reaction vessel is sized and structured to provide the desired dwell time for effectuating an initial solids/liquid separation by the sulfur dioxide of the treated wastewater. Where slurry transport is employed, minimal dwell time is required as discussed above so that the majority of the chemical dewatering occurs in the drying beds or mechanical separators.

In one embodiment, the wastewater transport inflow pipes themselves are used as a reaction vessel treatment zone for injected bottled $SO_2$. The pipe segment required for this sulfur dioxide treatment must be acid resistant to the acidified sulfur dioxide treated wastewater. If not, an acid resistant extender made of stainless steel or polypropylene or similar acid resistant material is attached to the end of the transport inflow pipes. The length and diameter of the inflow pipe segment required for treatment is selected to allow sufficient dwell time therein after sulfur dioxide injection to effectuate the initial desired solid/liquid wastewater separation. If disinfected solids/liquid wastewater is required, the reaction zone is sized to provide an approximate 20-minute dwell time at pH 2 until total disinfection is achieved.

At least one drain pad is positioned and structured to collect and drain the solids from the sulfur dioxide treated wastewater. These drain pads are constructed of an acid resistant material such as stainless steel, acid resistant cement or propylene liners. They have a large drying surfaces, which may be made of mesh or include drain holes or channels to direct the draining water to a point of collection for pH adjustment and reuse. The mesh or holes may be covered with a filtration cloth, such as a cotton or fiber sheet, to aid in separating the solids. Cotton sheets have the advantage of not having to be removed before burning the dried solids as their air emissions from burning are approximately the same as the dried solids.

The drain pads are structured to hold the separated solids until the desired chemical dewatering has occurred. Complete drying takes approximately 24 hours. However, a shorter drying time to produce solids with a higher water content for burning is often employed to provide a fuel with a higher BTU content. Usually, a series of drain pads are included so that at least one is being filled, while the others are draining the solids. Once the solids have drained sufficiently, they are removed via a front-end loader scraper and trucked for disposal. Preferably these drain pads are movable or rapidly constructed so that in the event of a flood emergency they may be relocated to higher ground.

The dried solids are then removed and disposed of with disposal means such as scrapers and loaders filling trucks for hauling the treated solids to a landfill. Alternatively, as the dried solids generally have a BTU content similar to wood, they may also be burned or gasified as a fuel. A mobile gasifier or boiler and electrical generator set, such as those produced by Thermogenics, Inc. of Albuquerque, N. Mex. may be employed for this purpose, or the solids transported to a more permanent stick built gasifier or electric generator for admixing with other fuels such as a fluidized coal bed electrical generator.

In another variation, the mobile equipment design uses a sulfurous acid generator to inject sulfur dioxide into the raw wastewater treatment plant inflows having a low solids concentration of approximately 1% until odor suppression results and the initial solids are conditioned for separation. A typical skid mounted sulfur generator producing hydrous sulfur dioxide such as those currently produced by Harmon Systems International, LLC of Bakersfield, Calif. are employed to simultaneously generate anhydrous sulfur dioxide for gas injection and mixing in a water tower. Sulfur burners also have the advantage of minimizing $SO_2$ release from explosion in the event of terrorist attack of the wastewater treatment plant.

Usually conditioning occurs at a pH of approximately 2 or lower. At this point, wastewater odors are eliminated, and the solids change color from a dark brown to a light grey and are more fibrous. These conditioned solids are then separated by passing them through the pores of a woven polymer bag placed on a drain pad, whose weave porosity is selected for rapid draining of excess water from the solids. The sulfur dioxide treated wastewater is thus rapidly pumped directly into the woven polymer bag where the remaining chemical dewatering occurs without the need for further drying or treatment. The treated separated water is then collected on the drain pad and land applied in alkaline soil areas, or further treated with an alkaline reagent, such as lime for heavy metals removal or pH adjustment to meet permit discharge requirements.

Drain bags may be mandated by those communities requiring covered solids containment. These drain bags have a mesh sized to collect and separate the treated solids from the treated wastewater drains through the drain bag onto the drain pad and into a collection system associated with the drain pads. The filled drain bag is then disposed of generally via landfill, or burned or gasified. Polypropylene bags such as those produced by Miratech a division of Ten Cate Nicolon of Pendergrass, Ga. provide a bag, which is acid resistant, and prevents bird vector transport of the solids. Depending upon the air emissions standards, these drain bags may or may not have to be separated from the dried sludge solids contained therein before burning or gasification.

Anhydrous and hydrous sulfur dioxides are strong disinfectants. When employed, they disinfect both the liquids and solids fractions to provide liquid handling and solids storage without the emissions of odors. The recovered sulfur dioxide-treated wastewater therefore does not have viable competing organisms when used for growing algae. Sulfur dioxide is relatively cheap and readily available. It may also be generated on-site from the burning of raw sulfur; particularly if additional heat from sulfur burning is required for solids process drying. Sulfur dioxide is extremely hydrophilic and forms sulfurous acid on contact with water. Injection until an elevated pH of approximately 2 for approximately 30 minutes results in complete disinfection; see Adams et al., U.S. Pat. No. 4,340,489. This sulfurous acid concentration is approximately that of lemonade and does not expose an operator to injury.

For batch separation, after the initial approximately half hour solids conditioning and separation, the sulfur dioxide treated solids have a moisture content of 30% to 40% and continue to shed water on a drying venue, such as a drain bag, etc. for approximately 24 hours, ultimately reaching the consistency and dryness of wood with a 1 to 4 percent by weight water content. This dried product may then be land filled, burned, or gasified in a manner consistent with the treatment plant unit processes and/or permit constraints.

Thus, the wastewater treatment method may be employed in various types of modular apparatus sized and expanded as needed to avoid the carrying costs of conventional mechanically concentrated systems constructed with excess capacity to meet projected future wastewater treatment needs. Chemical dewatering equipment has a much lower installation cost, which can be leased or installed on a pay as you go basis at a wastewater treatment site. For example, instead of the $26,500,000 price for installing a typical 10 MGD conventional plant to provide optimal economy of scale operating costs (assuming full capacity usage), an under $1,000,000 modular sulfur dioxide/liming package unit may be added to a plant's existing footprint to provide a 0.5 to 1 MGD incremental hybrid chemical/mechanical/biological dewatering system. Additional 0.5 to 1 MGD modules may then be added and installed as needed. The concentrated solids are then disposed of in accordance with permitting requirements.

For example, for those plants land filling treated solids, such as the Central Valley Water Reclamation Facility in Salt Lake City, Utah, after retrofit with a modular sulfur dioxide/liming package units, the solids generated from this package dewatering equipment reduces landfill treated solids for disposal. The water content of the Central Valley Water Reclamation Facility's mechanically separated solids is typically 40% by weight. Employing instead the package dewatering system method results in treated solids having a 4% by weight composition, results in a net 36% by weight savings. The more concentrated sulfur dioxide dewatered solids should therefore reduce the present plant disposal costs of approximately $32.00/ton by about 36%. In addition, the reduced volume of treated solids extends the life of the present landfill facility by requiring less space to dispose of these more concentrated solids. Other savings from chemical dewatering result from avoiding the costs of polymers employed in more expensive conventional treatment plants, which typically average 9 pounds per ton of processed sludge as well as the reduced use of its belt presses. Off-setting these cost savings are the added costs of sulfur dioxide.

The amount of $SO_2$ is dependent upon the alkalinity and bicarbonates of the wastewater inflows, which generally is no more than 800 mg/liter (Standard Methods, 14$^{th}$ Ed. APHA, 1975); see Reynolds, U.S. Pat. No. 4,304,673. Reynolds found that generally no more than 2000, and preferably no more than about 600 mg of SO2 per liter of wastewater was required.

Using 1 liter equals 0.2641721 gallons and 1 mg=$\frac{1}{1000}$ gr., 1 gr.=$2.204623 \times 10^{-3}$ pounds; for a 0.5 MGD plant this equals:

0.5×1,000,000 gallons/day×1 liter/0.2641721 gallons× 2000 mg/liter×1 gr/1000 mg×0.26417212 gallons/liter× 2.204623×10−3 pounds/gram=2,204.6229 pounds/day or approximately 1 ton of sulfur dioxide under a worst case alkalinity scenario. It is expected that the 600 mg of $SO_2$ per liter is more realistic for most wastewaters, reducing the chemical treatment tonnage required by one third. Current pricing in dollars per ton of liquid bulk f.o.b. works currently is around $230/ton so that the chemical dewatering cost is relatively nominal. This sulfur dioxide may be delivered to the site in tanks, or generated on site via sulfur burners. Sulfur burners are relatively efficient and have the additional benefit of generating considerable heat from sulfur burning, which can be used to supply heat to the treatment plants drying beds.

The sulfurous acid leached heavy metals stripped from the conditioned solids enter the liquid phase as micronutrients to promote algae bloom (eutrophication). If the heavy metals are too concentrated for algae growth, they can be removed from the treated wastewater stream via the addition of CaO or hydrated lime before raising the algae or discharge into a stream or lake. This not only precipitates the heavy metals as metal hydroxides, but some insoluble calcium phosphates. These precipitates may be removed via filtration and sold or land filled.

For cost comparison, the sulfur dioxide chemically dewatered wastewater treatment method may also be adapted to generate added revenues from the gasification or burning of the concentrated high Btu solids for production of heat or electricity. In addition, there are added revenues from sales of the chemically demetalized and disinfected water sales, and the harvested algae. The plant or algae absorbed $CO_2$ also qualifies for carbon credits to reduce greenhouse emissions.

This wastewater treatment method may also receive revenues from soil conditioning services associated with the land application of the acidified sulfur treated wastewater. This is particularly important in alkaline soil regions where the additions of acids to soils is routinely required, thus providing an additional potential revenue stream to be factored in against the plant costs. $SO_2$ water conditioning also may be blended with the chlorine treated discharge from a conventional wastewater treatment plant to remove chlorine before land application.

As discussed above the pH adjusted filtrate is directed into a photo biomass/algae reactor for removing heavy metals, and reducing its BOD content producing a recovered treated wastewater. This recovered treated wastewater may be land applied particularly in areas of alkaline soils where acidified water is required for soil conditioning. If the heavy metals acid leached from the treated solids are too high for land application, these heavy metals in the treated wastewater may be removed by alkaline precipitation of the metals therein as metal hydroxides. These metal hydroxides are then removed via settling or filtration via belt presses or polypropylene bags.

If land applied, the calcium added lowers the Sodium Adsorption Ratio (SAR) and off-sets any sodium accumulation allowing the $SO_2$/sulfurous acid/bi-sulfite/sulfite treated wastewater to be safely applied to a wider range of soils including alkaline and high pH soils and to maintain and/or improve their existing soil fertility. Thus, this recovered treated wastewater with its high calcium content, ammonia and plant nutrients, the ability to lower the pH of alkaline soil by delivering additional acidity into the soil, and for its properties to reduce and suppress soil pathogens, etc., can be utilized to act as a soil amendment and to be a source of valuable plant nutrients. This method provides treated wastewater nutrients of consistent composition particularly suited for aquaculture to raise aquatic plants, algae, and other photo biomass microorganisms. This photo biomass/algae further conditions the recovered treated wastewater making it particularly suited for the propagation of crops (where and whenever its use is allowed), as biological means to utilize and remove these constituents, in the same manner as claimed and disclosed in co-pending patent application, Harmon et al, entitled "Wastewater Chemical/Biological Treatment Method and Apparatus, Ser. No. 12/286,083 filed Sep. 26, 2008.

However, in one wastewater treatment method, the treated conditioned wastewater is processed by algae to utilize and biologically reduce the dissolved solids and ammonia (for BOD compliance). Nutrients like nitrogen (N), phosphorus (P), and potassium (K), are important for algae plant growth and are essential parts of fertilizer. Silica and iron, as well as several trace elements, may also be considered important marine nutrients as the lack of one can limit the growth of, or productivity in, an area. These nutrients are all present in wastewater from the treatment of sewage, agricultural, or flood plain run-off, if disinfected properly to minimize health risks and prevent growth of unwanted strains of competing micro-organisms.

One variation of the present invention disinfects saline separated wastewater using sulfur dioxide, and is then pH adjusted to neutralize the toxic effects of the sulfur dioxide by converting it to sulfates, at a pH level required for algae growth. The saline wastewater is conditioned and pH adjusted after sulfurous acid treatment to a brine level suitable for algae production as feedstock for biosynthetic fuels. This produces a method of disposal and reuse of saline wastewater for the production of biosynthetic fuels by employing biosynfuels processes, such as the process developed by Environmental Bio-Fuels, Inc. of Bountiful, Utah, which doesn't require the algae to be dried to a powder consistency before conversion into a biosynfuel. The advantage of growing biosynthetic fuels is that they sequester carbon dioxide and avoid potential microbial transfer to edible crops. Algae growth can be promoted by running stack gas from combustion burning through the wastewater. In addition, wastewaters are often too saline for raising conventional crops, but are particularly suitable for raising certain types of algae. Also, heavy metals present in wastewaters often promote algae bloom; thereby increasing yields.

In summary, the above wastewater treatment method and apparatus provides the following advantages:

Water Savings

One advantage of this improved wastewater treatment method is its reduced process water loss, and double use of the water to grow first biomass feedstock, leaving recovered treated wastewater with reduced BOD's and heavy metals for growing conventional crops. This wastewater treatment process is much faster than conventional mechanical dewatering systems so evaporation losses are reduced. Conventional mechanical concentration systems are most successful in areas where the excess wastewater is evaporated into the atmosphere in hotter more arid regions. Unfortunately, this evaporative consumptive use of water in and regions is now becoming a conservation issue. Presently on the Jordan River system in Salt Lake City, Utah, various sewage treatment plants are seeking to claim water rights to the treated waters exiting their plants and divert and sell the same to different water drainages to off-set costs. These water right claims for the first time in Utah will indirectly establish the cost of evaporative consumptive use of water related to sewage treatment operations so that evaporated lost water now becomes a cost of operations. Not only is water lost through evaporation, but the high water content in the land filled sewage must also be factored in. Hence, future mechanical concentration wastewater treatment systems must factor in the lost process water consumption as a cost in evaluating the best sewage treatment mode as the volume entering the plant and leaving the plant is easily quantifiable and affects future water right claims.

The additional water generated from this method often provides a significant amount of additional water, while maintaining the same treated water output for downriver users and habitat enhancements. This avoids plant operating dictates from downriver users who have vested rights to existing treatment water outflows.

Crop Land Savings

Using photo biomass/algae bioreactors to produce biofuel feedstock from wastewater avoids the need to tie up valuable farm lands to raise biofuel feedstock to produce biofuels, such as ethanol. Consequently more agricultural land is freed up for raising food crops insuring their economic availability.

Eutrophication

Other environmental clean-up advantages result, such as minimizing stream eutrophication as the induced photo biomass/algae bloom and recovery removes micronutrients before stream discharge and absorbs many of the heavy metals. Present mechanical concentration methods have focused on banning phosphate detergent usage, and removing phosphates from farm, and industrial sources entering wastewater streams before discharge to prevent eutrophication. These phosphate removal costs are significant, and fail to factor in the eutrophication impacts of heavy metals. The Swedish Phosphate Report concluded that removal of phosphates from detergents was pointless and ill advised. Water pollution was a far more complex problem than early environmental activists had assumed and it was proven to depend on a variety of factors, among which phosphate was perhaps one of the least important. The main cause was demonstrated to be industrial pollution by heavy metals, oils and insecticides, as all these substances kill the zooplankton that feed on the algae causing the problem; see *The 13th Element*, by John Emsley, John Wiley & Sons, 2000, at page 273, Chapter "Oh Shit". The removal of heavy metals and some phosphates by the algae in the hybrid chemical, mechanical, biological dewatering system thus results in significant environmental benefits.

Organic Chemicals

This improved wastewater treatment process employs sulfurous acid in combination with lime to condition and grow photo biomass/algae. Both of these chemicals are naturally occurring and classified as organic substances by the National Organic Standards Board. Combined with naturally occurring photo biomass/algae treatment, the plants are safe to operate and do not generate dangerous emissions.

Separated Solids Fuel

Most mechanical dewatering methods generally produce sludge with high 30-40% water content as outlined above.

This high water content prevents direct burning. Consequently, mechanically dewatered high water content sludges are admixed with other fuels, such as coal, for burning or gasification because of their high water content. Alternatively, they must first be further dewatered via drying beds and dryers, which add to their fuel processing costs. Generally, it has been found that these mechanical dewatered sludges seldom have enough independent fuel value to justify the drying cost for use on-site at smaller facilities and must be disposed of using other methods, such as land filling or admixing with other fuels for burning.

Conversely, chemically dewatered sludge produced by injecting either gaseous $SO_2$ or aqueous $SO_2$ (sulfurous acid) provide solids with low water content and a relatively high BTU low sulfur concentrated fuel suitable for burning or gasification to produce heat, electricity, or other forms of useful energy, such as steam. The sulfur dioxide dewatering method produces a fuel with a fairly consistent BTU content dependent upon the raw product composition. For example, one chemically treated and separated sludge generated near Logan, Utah produced a chemically dewatered densified fuel having a BTU content similar to wood of between approximately 7,040 BTU/lb. ASTM (American Society Testing Method) 02382 and 7,290 BTU/lb. ASTM 02382. Initial separation took place in one half hour after injection of gaseous SO2 having an initial 30% to 40% moisture content. If allowed to continue to completely dry over a 24 hour period, a moisture content of between 4% to 6% was achieved. This chemically dewatered sludge had the appearance, and texture similar to dark dry wood. It was essentially odorless with a moisture content of between 4% and 6%. It had a high cellulose solid content of between 94% and 96% similar to wood making them readily transportable and storable until burned or gasified. This dry wood like sludge had approximately 1.8% by weight $SO_2$ emissions, when burned, which is comparable to those produced by low sulfur coal. Depending upon the fat content of the solids in the wastewater, the treated solids may have even a higher BTU content than wood. Consequently, the by-product fuel of chemically dewatered concentrated sludge may be burned directly, and/or admixed with the mechanically separated sludge for burning or gasification.

Photo biomass/Algae Credits

The nutrient rich conditioned wastewater may be used to raise photo biomass/algae for harvesting to provide a continuous source of biofuel feedstock, or may be used for cosmetics, or other uses as a side benefit. Photo biomass/algae rapidly assimilates $CO_2$ as part of its growth processes, so if used as a biofuel, the improved wastewater treatment processing qualifies not only for biofuel credits, but carbon credits as well. These carbon and biofuel credits provide added revenue off-sets to a wastewater treatment plant's operating costs.

Soil Conditioning

In arid regions where alkaline soils are often found, the method may generate acidified wastewater discharge to provide soil conditioning benefits, which reduce nutrient and water agricultural demands by making the soil more porous. In addition, instead of removing chemicals via competing membrane technologies, a balanced chemical composition is generated with this wastewater method to grow algae, thus providing, an additional revenue source for this land conditioning method.

Community Preferences

Intangible aesthetic factors often drive the selection of a sewage treatment technology in those areas abutting urban development. The present method provides an odorless plant, the production of biofuel feedstock, carbon credits, lower operating costs, removal of heavy metals, pathogen kill, inactivation of pharmaceuticals in the wastewater gathering system, and reduced plant size. Although these intangible factors are often subjective, they are often the controlling factors in mandating the type of wastewater treatment design.

Plant Security

The smaller treatment plant footprint enables better plant security as there is less area to patrol and protect. The employment of mobile units, which can readily be replaced and moved, also provides shorter replacement time in the event of a disaster or incident. Also, emergency flooding can be anticipated and the treatment plant location varied to avoid flooding of large settling lagoons and the resultant contamination to the surrounding areas.

SUMMARY

The sulfur dioxide chemical/mechanical/biological wastewater treatment method and apparatus employ organic chemicals to optimize wastewater treatment by employing the advantages of both chemical and mechanical separation and biological treatment techniques to propagate and recover of photo biomass/algae to reduce BOD's and heavy metals to produce recovered treated wastewater suitable for raising crops and vegetation or open waster discharge.

DESCRIPTION OF THE ILLUSTRATED EMBODIMENTS

Figure 1:
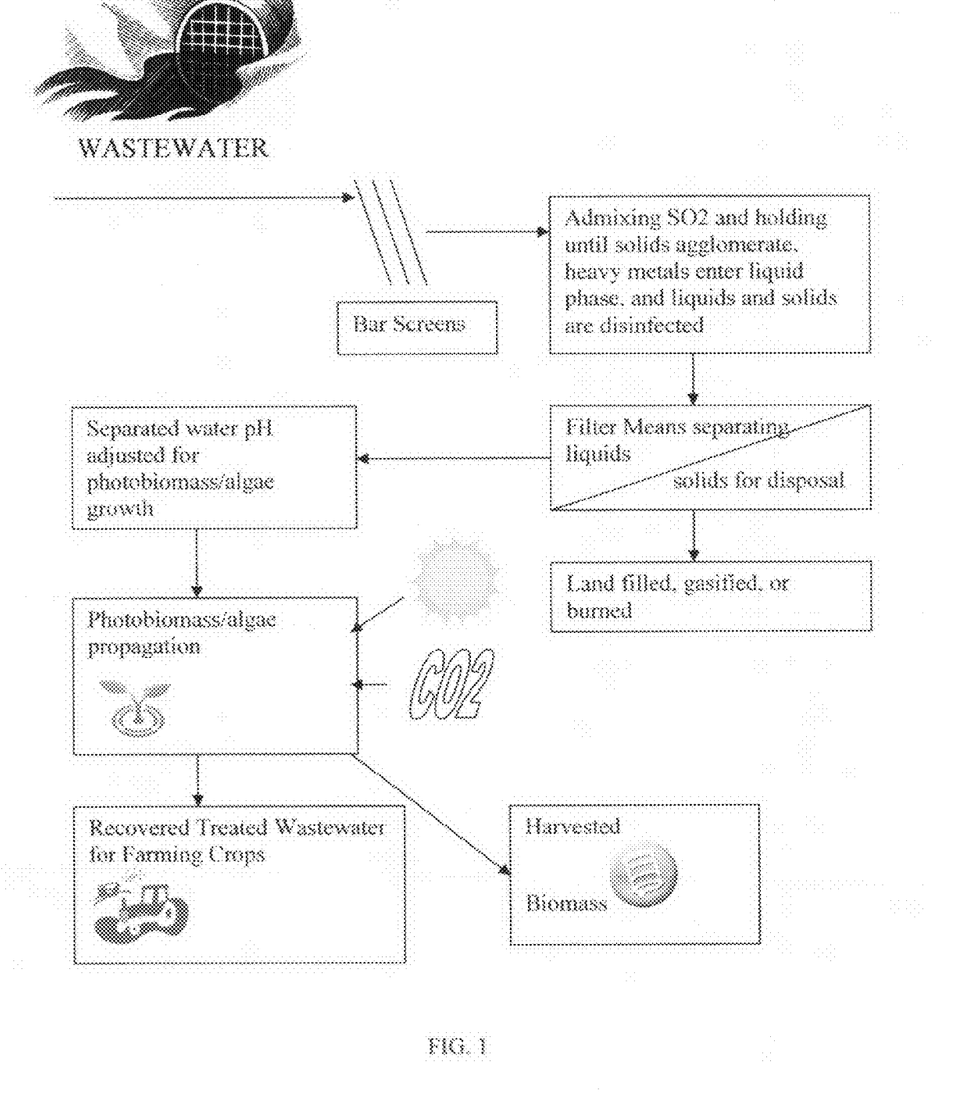
FIG. 1 illustrates a typical the layout of the wastewater treatment method.

FIG. 1 illustrates a typical layout of the wastewater treatment method disinfecting and adjusting the recovered treated wastewater for photo biomass/algae propagation. The wastewater is screened to remove courser solids before admixing sulfur dioxide into the screened wastewater. The sulfur dioxide-treated screened wastewater is held until the solids agglomerate, heavy metals are acid leached from the solids into the liquid phase, and the liquids and solids are disinfected. The sulfur dioxide-treated screened wastewater is then passed through filter means to separate the solids for disposal from the sulfur dioxide treated liquids containing disinfected plant nutrients. The sulfur dioxide-treated liquids are then pH adjusted to the pH required to grow photo biomass/algae. The pH adjusted sulfur dioxide-treated liquids are then sent to a bioreactor containing photo biomass/algae. Sunlight and carbon dioxide are then admixed with the nutrients in the pH adjusted sulfur dioxide-treated liquids to grow the photo biomass/algae, which is periodically harvested. The recovered treated wastewater is then used to raise crops.

Figure 2:
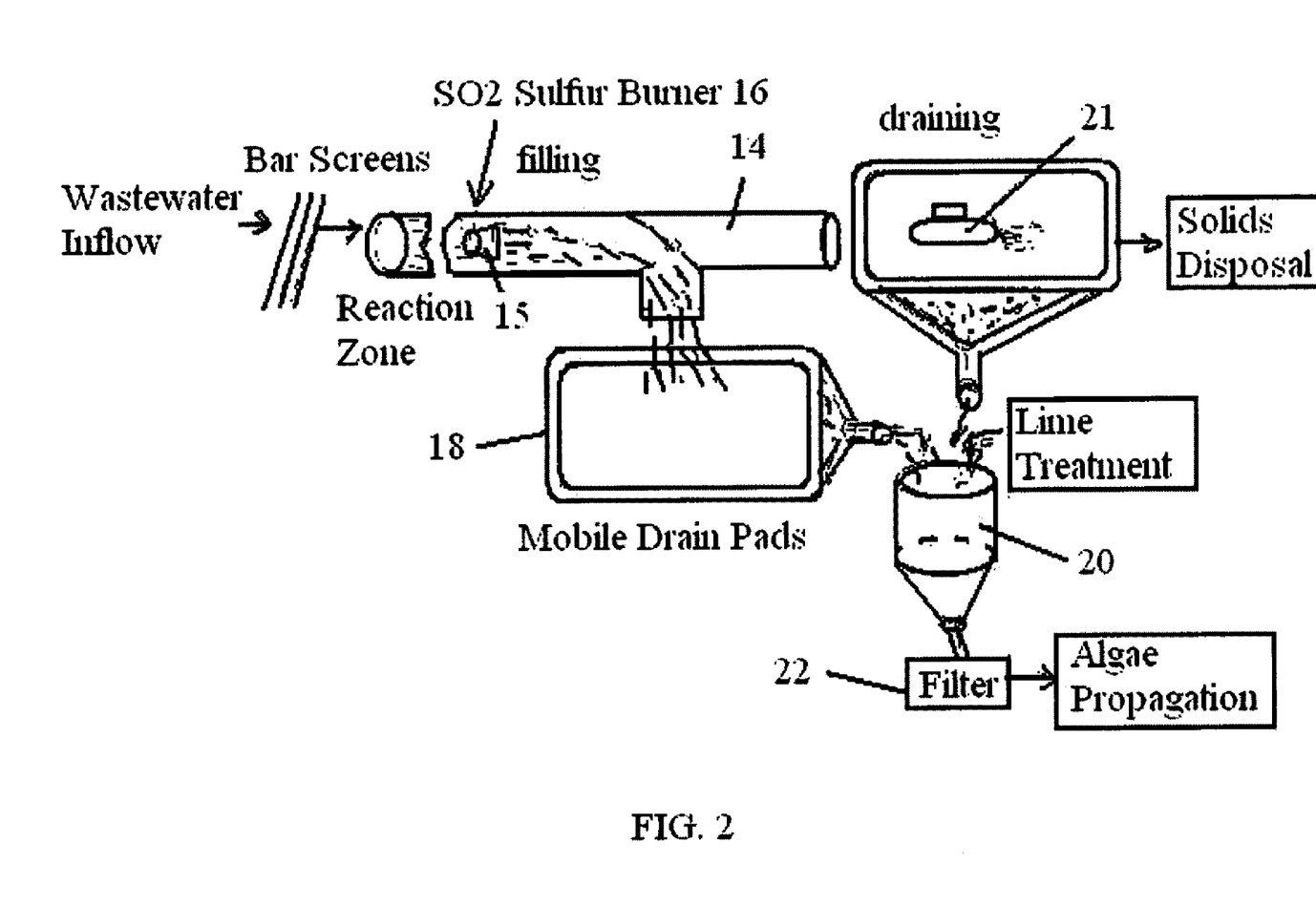
FIG. 2 illustrates a preferred layout of the wastewater treatment equipment to condition recovered treated wastewater for growing photo biomass/algae.

FIG. 2 illustrates the simplest embodiment of a skid mounted sulfur dioxide wastewater treatment plant 10. The influent wastewater inflows are preliminarily screened with bar screens 12 before entering a reaction vessel 14 structured as a serpentine polyurethane acid resistant pipe 14. The serpentine pipe 14 may have a gas diffusion mixer 15 mounted therein to admix sulfur dioxide from a skid mounted sulfur burner 16 to separate the solids from the liquids by agglomeration. Or, the sulfur burner 16 itself may be used to admix sulfur dioxide into the wastewater streams where the solids concentrations are fairly low (1 to 3% by weight). The wastewater microorganisms are killed by the $SO_2$ exposure to prevent competing with the algae. The serpentine pipe 14 is flexible and has a T-bend with valve 17 to direct the separating fluid mixture onto mobile drain pads 18. At least two mobile skid mounted pads 18 are included so that as one is filling, the other is draining. These pads 18 separate and hold the solids, while allowing the treated wastewater to drain into the pH adjustment and separation collection vessel 20.

After drying, the solids are scraped from the pads 18 with a scraper 21 for hauling and land filling.

The sulfur dioxide-treated wastewater is collected in a pH adjustment vessel 20 into which lime is added to adjust the pH of the sulfur dioxide-treated wastewater to that required to raise algae. This alkaline-treated mixture is then passed through another filter 22 to remove any metal hydroxide cake from the treated water before algae propagation.

In the example shown in FIG. 2, the serpentine pipe 14 is sized to provide one half hour dwell time for the screened influent to provide sufficient dwell time for disinfection.

Figure 3:
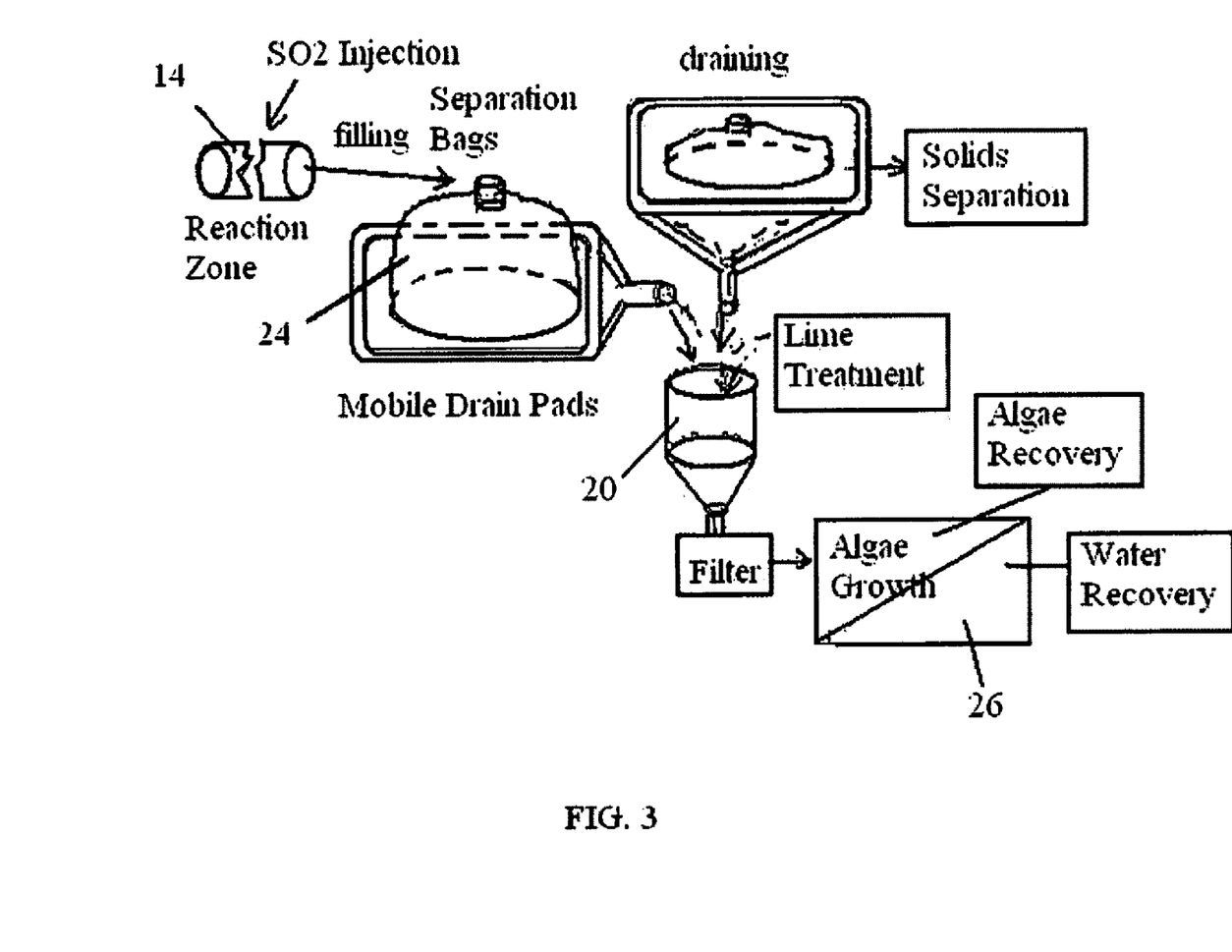
FIG. 3 illustrates a preferred layout of the wastewater treatment equipment employing separation bags for solids separation.

FIG. 3 illustrates the embodiment of FIG. 2 employing polyurethane woven separation bags 24 mounted onto mobile drain pads 18. Sulfur dioxide is injected into the wastewater streams until the solids agglomerate sufficiently to be held by the weave of the separation bags 24. If necessary, the treated wastewater streams are held in a treatment vessel (not shown), or a serpentine tube until the initial separation is accomplished. The separation bags 24 separate and hold the solids, while allowing the sulfur dioxide-treated wastewater to continue to drain into a collection vessel 20. The separation bags 24 also prevent access by birds and other animals while hiding from view the drying solids. When the separation bags 24 are filled with solids, which have completed draining, the filled separation bags 24 are removed for hauling and land filling or burning, and the filtered pH adjusted water is used to propagate algae in a bioreactor 26, which reduces BOD's and heavy metals concentration in the filtered water, which is then dumped into open streams, or used to raise crops.

Figure 4:
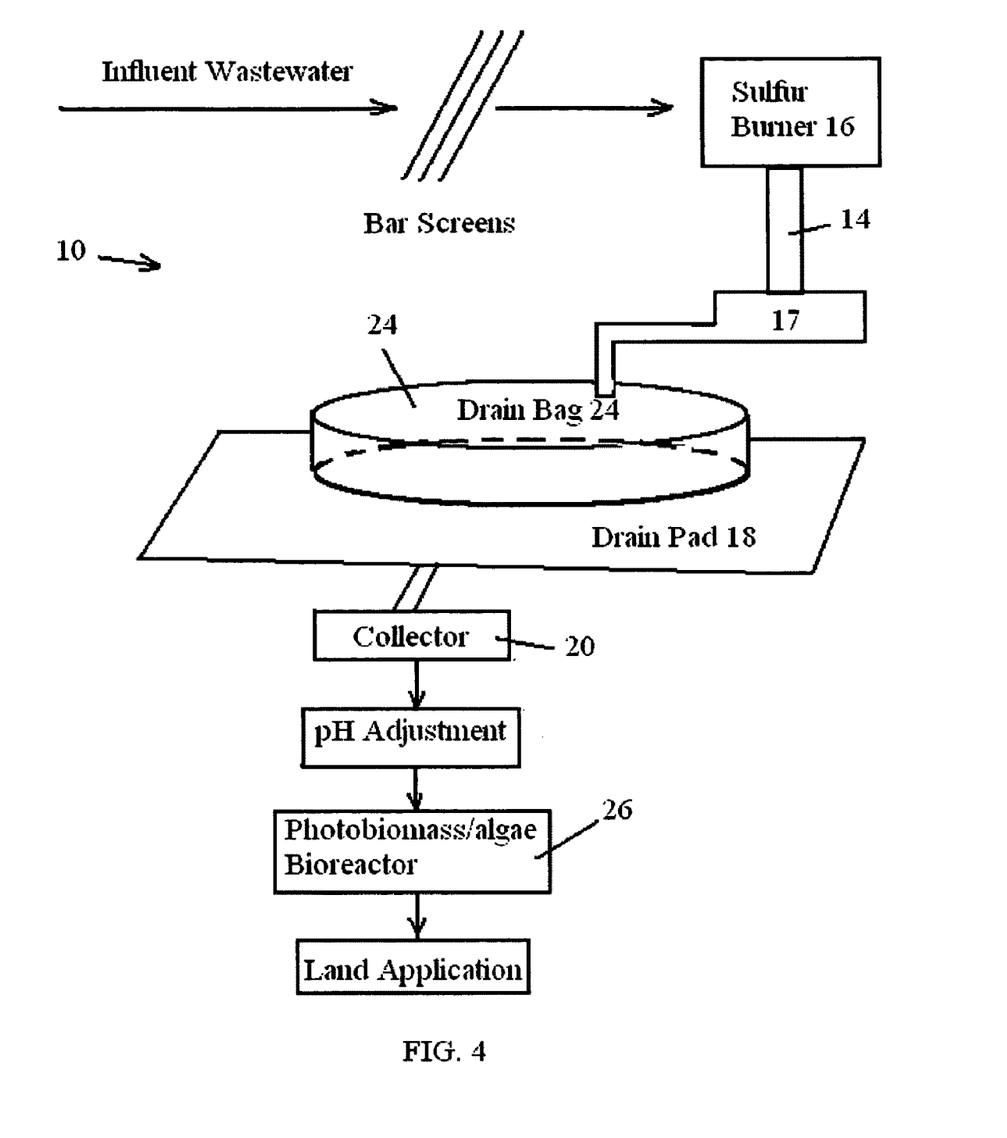
FIG. 4 illustrates a preferred embodiment of a chemical/mechanical dewatering system to separate solids.

FIG. 4 illustrates a preferred embodiment of a chemical/mechanical/biological dewatering system layout of a skid mounted sulfur dioxide wastewater treatment plant 10. The influent wastewater inflows of 1 to 3% solids by weight are preliminarily screened with bar screens 12 before entering a sulfur burner 16 which admixes sulfur dioxide into the wastewater inflows to initially separate the solids from the liquids by agglomeration into an approximately 3% concentration. The partially separated solids are then pumped through a flexible pipe 14 with a T-bend with valve 17 to direct the separating fluid mixture into a woven polymer bag 24 placed on a plastic sheeting drain pad 18 sloped for draining. These bags 24 separate and hold the solids for further dewatering in the bag up to 1 to 4% water by weight. The treated wastewater is collected on the sheeting pad 18 and deposited into a collection vessel 20 where the filtrate is pH adjusted for raising photo biomass/algae, such as algae in a bioreactor 26 to produce recovered treated wastewater for land application. After drying, the solids and bag are scraped from the plastic sheeting pads 18 with a scraper 21 for hauling and land filling.

The pH adjustment level is dependent upon the strain of the photo biomass/algae selected for use in the bioreactor 20. Usually a local algae used to growing in a given region is selected for use in the bioreactor. These local algae strains contain lipid oils and are often best suited to grow in the seasonal fluctuations in light, and temperature, and can be stimulated by adjusting their nitrogen and phosphorus nutrient ratios, as discussed in the article "Effects of N:P atomic ratios and nitrate limitation on algal growth, cell composition, and nitrate uptake" by G-Yull Rhee, JSTOR: Limnology and Oceanography, Vo. 23, No. 1 (January, 1978) p. 10. The advantage of using treated wastewater inflows entering a wastewater treatment plant as a growth media for the photo biomass/algae is that the nitrogen and phosphorus concentration levels are fairly consistent throughout the year, varying mainly with storm events. Consequently, their growth is not retarded by nutrient limitation; see "Nutrient control of algal growth in estuarine waters. Nutrient limitation and the importance of nitrogen requirements and nitrogen storage among phytoplankton and species of macro algae" by Morten Foldager Pedersen, Vol. 142:261-272, 1996 published Oct. 24, 1996 in Marine Ecology Progress Series. These local species thus provide viable strains, which may not have as many lipids as others, but their added growth volume makes them a preferred biomass feedstock.

Figure 5:
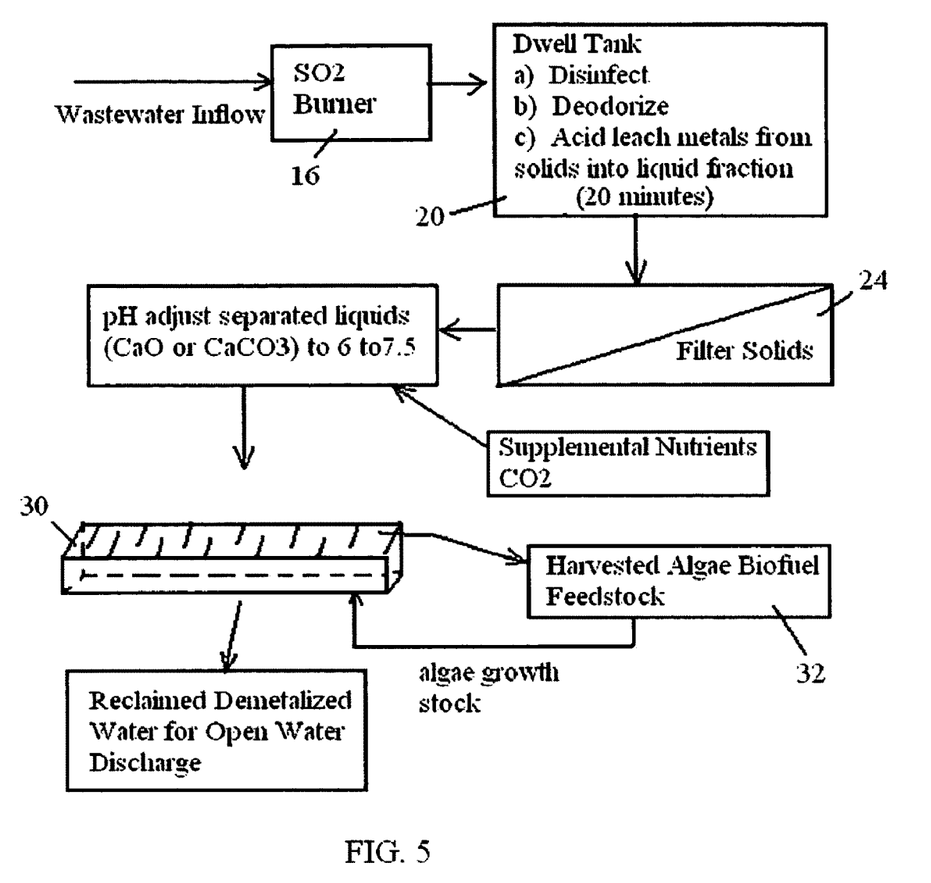
FIG. 5 illustrates another preferred embodiment of a chemical/mechanical/biological dewatering equipment layout.

FIG. 5 illustrates another preferred embodiment of the simplest chemical/mechanical/biological wastewater treatment method equipment layout wherein the screened influent wastewater is passed through a sulfurous acid generator 16 and injected with sulfur dioxide. The sulfur dioxide-treated wastewater is then held within a dwell tank 20 forming a slurry with minimal particle size for solids separation in a drain bag 24, which filters and separates solids for disposal or reuse. The sulfur dioxide-treated liquids are held in the dwell tank 20 until they are disinfected, deodorized, and the metals on the solids are acid leached into the liquid fraction. Usually this takes about 20 minutes, at a pH of approximately 2. The disinfected treated liquids are then pH adjusted with lime or limestone in a pH adjustment tank 28 to a pH of 6 to 7.5 to eliminate the biocidal properties of the sulfur dioxide and provide nutrients at a pH promoting algae growth. The exact pH is similarly selected as discussed, depending upon the algae strain to be propagated. Supplemental nutrients, and additional $CO_2$ from stack gas may be added to the pH adjustment tank 28

The pH adjusted treated wastewater is then delivered to an open pond or other algae propagation system 30, such as a shallow algae pond with a serpentine track, which exposes the algae to light to promote photosynthetic growth. Wastewater treatment evaporative or aquifer recharging ponds provide shallow impoundments, ideally suited for growing algae. They are seeded with local rapidly growing spores, such as blue-green algae, which have higher growth rates than other algae, and may be unlined, or lined, depending upon whether the treated wastewater is to be recovered for reuse. These ponds are sized and structured so that the entering wastewater streams with nutrients are gradually added to provide slow moving waters, which promote algae growth by avoiding turbidity, which stirs mud to the surface blocking sunlight exposure. These shallow impoundments allow sunlight to enter their top layers to heat the ponds, while providing energy for photosynthesis. If stack gas is used to add carbon dioxide to promote algae growth in the ponds, the heat from the stack gas also heats to ponds to promote algae growth.

The ponds are thus operated to insure growth of the algae. The main factors affecting algae growth are a continuous supply of nutrients including nitrogen and phosphorus, temperatures above 25 degrees centigrade, adequate sunlight, minimal turbidity, and stable conditions. The pH adjusted sulfur dioxide-treated wastewater provides a continuous supply of nutrients, so that operator is left primarily to focus on the other factors. If the nutrients are not sufficient to encourage the growth of algae, nitrogen and phosphorus fertilizers and $CO_2$ may be added.

Turbidity can be avoided and stable conditions built in to the plant design by regulating inflow rates of the nutrients. Lined ponds also prevent particulate matter from rising and circulating to block the light.

Temperature and light exposure are subject to environmental locations, and can be enhanced, if necessary, by heating the ponds and adding additional artificial light exposure. Thus locations in tropical regions are ideal to ensure algal blooms throughout the year.

Selection of algae species, such as blue-green algal cells, which contain gas vesicles that can be inflated or deflated to regulate their position within the pond to increase exposure to light, optimizes the light available for algae blooms. These blue-green algae prefer stable water conditions with low flows, long retention times, light winds and minimal turbulence. Baffles, weirs and barriers may be employed to decrease the flows of the treated wastewater in the ponds to promote algae growth. Shallow ponds also minimize thermal stratification to provide a more stable upper layer to encourage the growth of blue-green algal blooms.

The algae specie selected is preferably one, which does not generate harmful chemicals, which could affect safety in operating the wastewater treatment facility. Also, freshwater algal species that are present for extended periods and normally occur where water movement is minimal are preferred.

After the algae bloom occurs, it is then periodically collected and harvested via a floating bather (not shown) for biofuel feedstock, cosmetics, etc. Alternatively, conventional filtration means may be employed, such as pumping the top algae layers through porous woven bags 32, which separate the larger growth, but allow smaller algae spore organisms to pass through for reseeding the algae propagation system 30.

Water exiting the algae propagation system 30 is demetalized, and the nutrients consumed forming a water suitable for open water discharge or agricultural use.

In summary, the invention provides a package sulfur dioxide chemical/mechanical/biological sewage treatment plant and method employing rapid sludge chemical dewatering technology in conjunction with slower conventional mechanical dewatering solids agglomeration and bioreactors to meet cost, environmental permitting restrictions and other siting and permitting limitations for treatment and disposal of sewage and wastewater.

Although this specification has made reference to the illustrated embodiments, it is not intended to restrict the scope of the claims. The claims themselves recite those features deemed essential to the invention.

We claim:

1. A treatment method for a wastewater stream containing solids and liquids with organic and macronutrients suitable for growth of plants, algae, and photo biomass, comprising:
   a. injecting sulfur dioxide into the wastewater stream
   b. holding the sulfur dioxide-treated wastewater stream for the dwell time required to partially agglomerate wastewater solids, acid leach any heavy metals from the solids into wastewater stream liquids, and disinfect the wastewater stream liquids,
   c. separating solids for disposal or reuse from the sulfur dioxide-treated wastewater stream liquids,
   d. pH adjusting the sulfur dioxide-treated wastewater liquids to reduce the biocidal properties of any free $SO_2$, bi-sulfite, and sulfite and provide a pH required for environmental biological treatment, and
   e. passing the pH adjusted sulfur dioxide-treated wastewater liquids through an environmental biological system to grow unicellular and multicellular photoautotrophic, mixotrophic and paraphyletic and polyphyletic forms, and photobiomass including seaweeds, and cyanobacteria and photosynthetic bacteria as well as aqueous photosynthetic plants suitable for consuming nutrients from wastewater and use as a biofuel feedstock for separation and reuse, and reduce dissolved solids, heavy metals, nutrients, phosphorus and ammonia compounds in the wastewater liquids to provide recovered treated wastewater for reuse.

2. A treatment method for wastewater streams according to claim 1, wherein the unicellular and multicellular photoautotrophic, mixotrophic and paraphyletic and polyphyletic forms, and photobiomass including seaweeds, and cyanobacteria and photosynthetic bacteria as well as aqueous photosynthetic plants suitable for consuming nutrients from wastewater and use as a biofuel feedstock is selected to provide recovered treated wastewater meeting applicable open water discharge limits.

3. A treatment method for wastewater streams according to claim 1, wherein the pH adjusting uses calcium oxide or lime to adjust the calcium levels in the recovered treated wastewater to meet soil SAR conditions for land application to raise vegetation.

4. A treatment method for wastewater streams according to claim 1, wherein the environmental biological system includes algae, which is separated as feedstock for making biofuel, making cosmetics, and making fertilizers.

5. A treatment method for wastewater streams, according to claim 1, wherein the wastewater streams are selected from the group consisting of wastewater inflow streams entering a wastewater treatment plant and resulting outflow wastewater streams from the wastewater treatment plant's processing steps.

6. A treatment method for wastewater streams according to claim 5, further comprising the steps of filling and seeding a wastewater treatment plant's de-activated aerobic and anaerobic digesters and ponds with photo biomass/algae for generating revenues from:
   i. the production and sales of unicellular and multicellular photoautotrophic, mixotrophic and paraphyletic and polyphyletic forms, and photobiomass including seaweeds, and cyanobacteria and photosynthetic bacteria as well as aqueous photosynthetic plants suitable for consuming nutrients from wastewater and use as a biofuel feedstock, cosmetics, and other uses,
   ii. sales of treated recovered wastewater, and
   iii. sales of carbon and biofuel credits.

7. A treatment method for wastewater streams, according to claim 1, including adding supplemental nitrogen and phosphorus nutrients to the sulfur dioxide-treated wastewater to increase unicellular and multicellular photoautotrophic, mixotrophic and paraphyletic and polyphyletic forms, and photobiomass including seaweeds, and cyanobacteria and photosynthetic bacteria as well as aqueous photosynthetic plant growth.

8. A treatment method for wastewater streams according to claim 1, wherein $CO_2$ is injected into the sulfur dioxide-treated wastewater to increase algae growth.

9. A treatment method for wastewater streams according to claim 1, wherein separating the solids comprises passing the sulfur dioxide-treated wastewater through acid resistant porous bags with a mesh sized to collect and separate the sulfur dioxide-treated solids from the sulfur dioxide-treated wastewater placed on a drain pad structured to receive filtrate from the drain bags for subsequent use.

10. A treatment method for wastewater streams according to claim 9, wherein the drain pad is movable as needed to treatment locations above flood zones.

11. A treatment method for wastewater streams according to claim 1, wherein the unicellular and multicellular photoautotrophic, mixotrophic and paraphyletic and polyphyletic forms, and photobiomass including seaweeds, and cyanobacteria and photosynthetic bacteria as well as aqueous photosynthetic plants are selected to consume heavy metals contained in the sulfur-dioxide treated wastewater, leaving a demetalized treated wastewater for reuse.

12. A treatment method for wastewater inflow streams according to claim 11, wherein the demetalized treated wastewater is disposed of in water to dilute further its heavy metal concentration.

13. A treatment method for wastewater streams according to claim 1, further comprising the step of applying the recovered treated wastewater to land and thereafter raising crops on said land.

14. A treatment method for wastewater streams according to claim 13, wherein said crops are suitable for subsequent conversion to biofuels.

15. A treatment method for wastewater streams according to claim 13, wherein the recovered treated wastewater is acidified for absorption into the ground.

16. A treatment method for wastewater stream inflows entering a wastewater treatment plant or treated wastewater streams resulting from a wastewater treatment plant's processing steps containing solids and liquids with organic and macronutrients suitable for growth of plants, algae, and photo biomass, comprising:
   a. injecting sulfur dioxide into the wastewater stream inflows or treated wastewater streams resulting from a wastewater treatment plant's processing steps,
   b. holding the sulfur dioxide-treated wastewater inflows and streams for the dwell time required to partially agglomerate wastewater solids, acid leach any heavy metals from the solids into the wastewater stream liquids, and disinfect the wastewater stream liquids,
   c. separating solids for disposal or reuse from the sulfur dioxide-treated wastewater stream liquids,
   d. pH adjusting the sulfur dioxide-treated wastewater liquids with calcium oxide or lime to adjust the calcium levels in recovered treated wastewater to meet soil SAR conditions for land application to raise vegetation and reduce the biocidal properties of any free $SO_2$, bi-sulfite, and sulfite and provide a pH required for environmental photo biomass/algae biological treatment, and
   e. passing the pH adjusted sulfur dioxide-treated wastewater liquids through an environmental biological system to grow unicellular and multicellular photoautotrophic, mixotrophic and paraphyletic and polyphyletic forms, and photobiomass including seaweeds, and cyanobacteria and photosynthetic bacteria as well as aqueous photosynthetic plants for separation and reuse, and reduce dissolved solids, heavy metals, nutrients, and phosphorous and ammonia compounds in the wastewater liquids to provide recovered treated wastewater for reuse.

17. A treatment method for wastewater stream inflows entering a wastewater treatment plant or treated wastewater streams resulting from a wastewater treatment plant's processing steps according to claim 16, including raising vegetation suitable for subsequent conversion to biofuels with the recovered treated wastewater.

18. A treatment method for wastewater stream inflows entering a wastewater treatment plant or treated wastewater resulting from a wastewater treatment plant's processing steps according to claim 16, wherein the environmental biological system uses algae, which is separated and used as feedstock for making biofuel.

19. A treatment method for wastewater stream inflows entering a wastewater treatment plant or treated wastewater resulting from a wastewater treatment plant's processing steps according to claim 18, further comprising injecting sufficient carbon dioxide into the sulfur dioxide-treated wastewater to increase algae growth.

* * * * *